(12) United States Patent
Ramminger et al.

(10) Patent No.: US 11,474,045 B2
(45) Date of Patent: Oct. 18, 2022

(54) METHOD AND DEVICE FOR THE DETERMINATION OF FILM FORMING AMINES IN A LIQUID

(71) Applicant: Framatome GmbH, Erlangen (DE)

(72) Inventors: Ute Ramminger, Roth (DE); Ulrich Nickel, Erlangen (DE); Jörg Fandrich, Obermichelbach (DE)

(73) Assignee: FRAMATOME GMBH, Erlangen (DE)

( * ) Notice: Subject to any disclaimer, the term of this patent is extended or adjusted under 35 U.S.C. 154(b) by 141 days.

(21) Appl. No.: 17/043,001

(22) PCT Filed: Apr. 3, 2018

(86) PCT No.: PCT/EP2018/058438
§ 371 (c)(1),
(2) Date: Sep. 29, 2020

(87) PCT Pub. No.: WO2019/192673
PCT Pub. Date: Oct. 10, 2019

(65) Prior Publication Data
US 2021/0010943 A1 Jan. 14, 2021

(51) Int. Cl.
 *G01N 21/79* (2006.01)
 *G01N 33/18* (2006.01)
 (Continued)

(52) U.S. Cl.
 CPC ............. *G01N 21/79* (2013.01); *G01N 21/78* (2013.01); *G01N 31/221* (2013.01); *G01N 33/18* (2013.01);
 (Continued)

(58) Field of Classification Search
 CPC ....... C23F 11/141; G01N 21/78; G01N 21/79; G01N 31/22; G01N 31/221; G01N 33/18;
 (Continued)

(56) References Cited

U.S. PATENT DOCUMENTS 4,657,785 A 4/1987 Kelly et al.
6,099,801 A 8/2000 Lawrence et al.
(Continued)

FOREIGN PATENT DOCUMENTS

CA 1131002 A 9/1980
CN 101545885 A 9/2009
(Continued)

OTHER PUBLICATIONS

Stiller, K. et al, The Analysis of Film-Forming Amines—Methods, Possibilities, Limits and Recommendations, PowerPlant Chemistry, Waesseri GmbH, 2011, pp. 602-611.
(Continued)

*Primary Examiner* — Maureen Wallenhorst
(74) *Attorney, Agent, or Firm* — Dilworth IP, LLC

(57) ABSTRACT

A photometric method for determination of a concentration of a film forming amine in a liquid, including providing a buffer solution of a weak acid having a pKa≥4.5 and a strong acid having a pKa≤1; diluting an aliquot of the buffer solution with water, and determining the pH of the diluted buffer solution; adding reagent to the diluted buffer solution and measuring an initial absorbance of the diluted buffer/reagent solution; preparing a sample solution by adding liquid containing the film forming amine to an aliquot of the buffer solution and measuring the pH of the sample solution; adjusting the pH of the sample solution to match the pH of the diluted buffer solution by adding strong acid; and adding the reagent to the pH adjusted sample solution to form a colored complex, and measuring the absorbance of the resulting solution in a photometer.

10 Claims, 2 Drawing Sheets

(51) Int. Cl.
*G01N 31/22* (2006.01)
*G01N 21/78* (2006.01)
*C23F 11/14* (2006.01)

(52) U.S. Cl.
CPC ............ *C23F 11/141* (2013.01); *G01N 31/22* (2013.01); *G01N 33/1826* (2013.01); *Y10T 436/173845* (2015.01)

(58) Field of Classification Search
CPC .............. G01N 33/1826; Y10T 436/17; Y10T 436/173845
USPC .............. 436/106, 111, 163, 164; 422/82.05, 422/82.09
See application file for complete search history.

(56) References Cited

U.S. PATENT DOCUMENTS

| | | | |
|---|---|---|---|
| 10,315,234 B2* | 6/2019 | Ramminger | C23F 11/141 |
| 11,016,027 B2* | 5/2021 | Stuart | C23F 11/00 |
| 2011/0136704 A1 | 6/2011 | Sharma et al. | |
| 2014/0102481 A1 | 4/2014 | Ramminger et al. | |
| 2021/0123867 A1 | 4/2021 | Jasper | |
| 2021/0239620 A1* | 8/2021 | Trice | G01N 31/22 |

FOREIGN PATENT DOCUMENTS

| | | | |
|---|---|---|---|
| CN | 102131889 A | | 7/2011 |
| CN | 103940762 A | | 7/2014 |
| CN | 104596883 A | | 5/2015 |
| CN | 105283759 A | | 1/2016 |
| EP | 0562210 A1 | | 9/1993 |
| FR | 2463197 A1 | | 2/1981 |
| JP | H08294688 A | | 11/1996 |
| JP | 2008149226 A | | 7/2008 |
| JP | 2014145688 A | | 8/2014 |
| JP | 20200512548 A | | 4/2020 |
| WO | 2013127844 A1 | | 9/2013 |
| WO | 2014166542 A1 | | 10/2014 |
| WO | 2020/219754 | * | 10/2020 |

OTHER PUBLICATIONS

Lendi, M., Continuous Photometric Determination of Film-Forming Amines, PPChem, Waesseri GmbH, pp. 8-13, Jan. 1, 2015.
Evtushenko, Y. et al, Photometric Determination of Octadecylamine with Methyl Orange, Journal of Analytical Chemistry, vol. 57, No. 1, 2002, pp. 8-11.
Betova et al.: "Film-Forming Amines in Steam/Water Cycles—structure, properties, and influence on corrosion and deposition processes", Research Report, VTT-R-03234-14, Jul. 2014.
China Academic Journal Electronic Publishing House, Journal of Materials Protection, vol. 45. No. 3, Mar. 2012.

\* cited by examiner

METHOD AND DEVICE FOR THE DETERMINATION OF FILM FORMING AMINES IN A LIQUID

FIELD OF THE INVENTION

The invention is directed to a method and a device for the determination of film forming amines in a liquid, and in particular in the water-steam cycle of a nuclear power plant.

BACKGROUND OF THE INVENTION

Feed-water additives based on film-forming amines are used for the inside treatment or coating of pipelines, tubes or reactors in industrial plants to prevent those items against corrosion. Film-forming amines are typically polyamines or monoamines, such as fatty amines. The amines are specifically used as additives in water-steam cycles of a nuclear power plant to prevent corrosion of the inner surfaces used in the water-steam cycle.

WO 2013/127844 discloses a method for purifying and conditioning the circulation system of a power plant, especially the water-steam cycle of a nuclear power plant. According to said method, a film-forming amine is metered to the working medium circulating in the circulation system, wherein said film-forming agent forms a hydrophobic film on the inner surfaces of the circulation system. At least one measuring point is provided at the circulation system, and the concentration of the film-forming agent is monitored during operation of the purifying and conditioning process. Metering of the film-forming agent is stopped once its concentration in the working medium has reached a value of 1 ppm to 2 ppm at the at least one measuring point.

Treatments with film-forming amines are critical in relation to their concentration in the liquid working medium, which means that the concentration must be measured carefully to ensure a successful treatment or coating and to avoid unnecessary overdosing of the amines which may have undesired effects such as clogging of filters.

EP 0 562 210 A1 proposes a method for the simple and sensitive determination of polyamines in liquids, and a photometer for performing this method. A color formation of the polyamines in a sample is determined by a nearly monochromatic light coming from a conventional LED and filtered by a colored glass filter. The color forming reaction is based on the reaction of polyamines to be tested with rose bengal, wherein the reaction is performed in a pH buffered solution using acetic acid.

Yu. M. Evtushenko, V. M. Ivanov, and B. E. Zaitsev "Photometric Determination of Octadecylamine with Methyl Orange", Journal of Analytical Chemistry, Vol. 57, No. 1, 2002, pp. 8-11, disclose a similar method, wherein the reaction of the amine with methyl orange in water at a pH value of 2.5 to 4 was studied. The spectrophotometric determination of long-chain fatty amines using methyl orange is also specified in British Standard BS 2690: Part 117: 1983.

Katrin Stiller, Tobias Wittig and Michael Urschey in "The Analysis of Film-Forming Amines—Methods, Possibilities, Limits and Recommendations", PowerPlant Chemistry 2011, 13(10), describe the treatment concepts of water-steam cycles based on film-forming amines. Again, the studies on the determination of film forming amines are based on the use of the rose bengal method shown in EP 0 562 201 A1. The pH of the samples is kept between 2.3 and 3.3. It is shown that the method is very pH sensitive and that after the reagent addition, the pH of the sample must be absolutely between 2.3 and 3.3 to ensure reliable results of the concentration measurement of the amines.

WO 2014/166542 A1 proposes to determine the presence and concentration of a film-forming amine by reacting the amine with a reagent to form a colored complex, and by further adding a solution containing hydrochloric acid to lower the pH value of the sample solution containing the reagent and the film forming amine to a value which is lower than the pKa value of the reagent. Preferably, the pH value is lowered by adding hydrochloric acid to a pH of 2.3, preferably 2.0. In order to carry out the method, a sample of liquid containing the film-forming amine is introduced into a mixing chamber. An aqueous solution of a xanthene dye is added to the liquid in the mixing chamber, and at the same time hydrochloric acid solution is also added to lower the pH value to the sample solution in the mixing chamber to a value less than the pKa value of the xanthene dye. The sample solution containing the xanthene dye and the hydrochloric acid is then passed through a photometer, where the measuring is executed at a monochromatic wave-length in a range between 400 and 560 nm, depending upon the xanthene dye.

The known concepts for determining the concentration of polyamines in liquids include titration against methyl orange, or photometric measurement using eosin or rose bengal. However, these methods suffer from time consuming sample preparation or lack of accuracy.

On-line measurement methods disclosed in the patent literature are available as prototypes.

SUMMARY OF THE INVENTION

The object of the present invention is to provide an exact, fast and reproducible photometric determination of film forming amines with harmless reagents to monitor the course of amine concentration during amine applications at nuclear power plants with different regimes of the applied water chemistry.

The present invention solves this object by means of a method for the determination of a film forming amine in a liquid, wherein a reagent is added to the liquid to form a colored complex of the amine and the reagent, wherein the colored complex is measured photometrical, and wherein the method comprises the steps of
  a) Providing a buffer solution of a weak acid having a pKa≥4.5 and a strong acid having a pKa≤1;
  b) Diluting an aliquot of the buffer solution with a given volume of water, and determining a pH value of said diluted buffer solution;
  c) Adding a given amount of said reagent to said diluted buffer solution and measuring an initial absorbance of said diluted buffer solution containing the reagent;
  d) Preparing a sample solution by adding a given volume of the liquid containing the film forming amine to an aliquot of the buffer solution and measuring a pH value of the sample solution;
  e) Adjusting the pH value of the sample solution to match with the pH value of the diluted buffer solution by adding a calculated amount of the strong acid; and
  f) Adding a given amount of said reagent to the pH adjusted sample solution to form the colored complex and measuring the absorbance of the pH adjusted sample solution containing the reagent and the colored complex.

The inventors surprisingly found that when the pH value of the sample solution containing the film forming amine, prior to addition of the reagent, is adjusted and matched to the pH value of a reference solution for measuring the initial absorbance or transmission intensity of the reagent in the weak acid solution, the accuracy and reproducibility of the method can be markedly improved. Adjusting the pH value of the sample solution to match with the pH value of the reference solution prevents the measured absorbance from being distorted due to the dependency of the molar extinction coefficient of the reagent from the pH value of the solutions in the sample test cell and the reference test cell.

Photometric measurement of the colored complex in a weak acid solution also prevents the complex to undergo undesired side chain reactions. The pH adjustment can be done automatically using dosing equipment, or manually using a suitable graph or table. It is also possible to perform the method in an on-line measuring device to ensure a continuous monitoring of the film-forming amine in the process liquid.

Accordingly, the invention further provides a device for determining a film forming amine using the above method, wherein the device comprises
- a mixing chamber and a photometer connected to the mixing chamber;
- and a pH sensor provided in the mixing chamber; and
- a control unit connected to the mixing chamber and the photometer;
- wherein the mixing chamber is connected to a feedstock of a strong acid and water, and further comprises an inlet line for a buffer solution, an inlet line for a processing liquid and an inlet line for a reagent solution; and
- wherein the control unit comprises means for controlling an amount of the buffer solution, the processing liquid and the reagent solution supplied to the mixing chamber, as well as means for calculating and introducing an amount of the strong acid and water into the mixing chamber based on an input signal received from the pH sensor, and wherein the control unit further comprises means for calculating an amount of a film forming amine in the processing liquid based on an input signal received from the photometer.

DETAILED DESCRIPTION OF THE INVENTION

Figure 1:
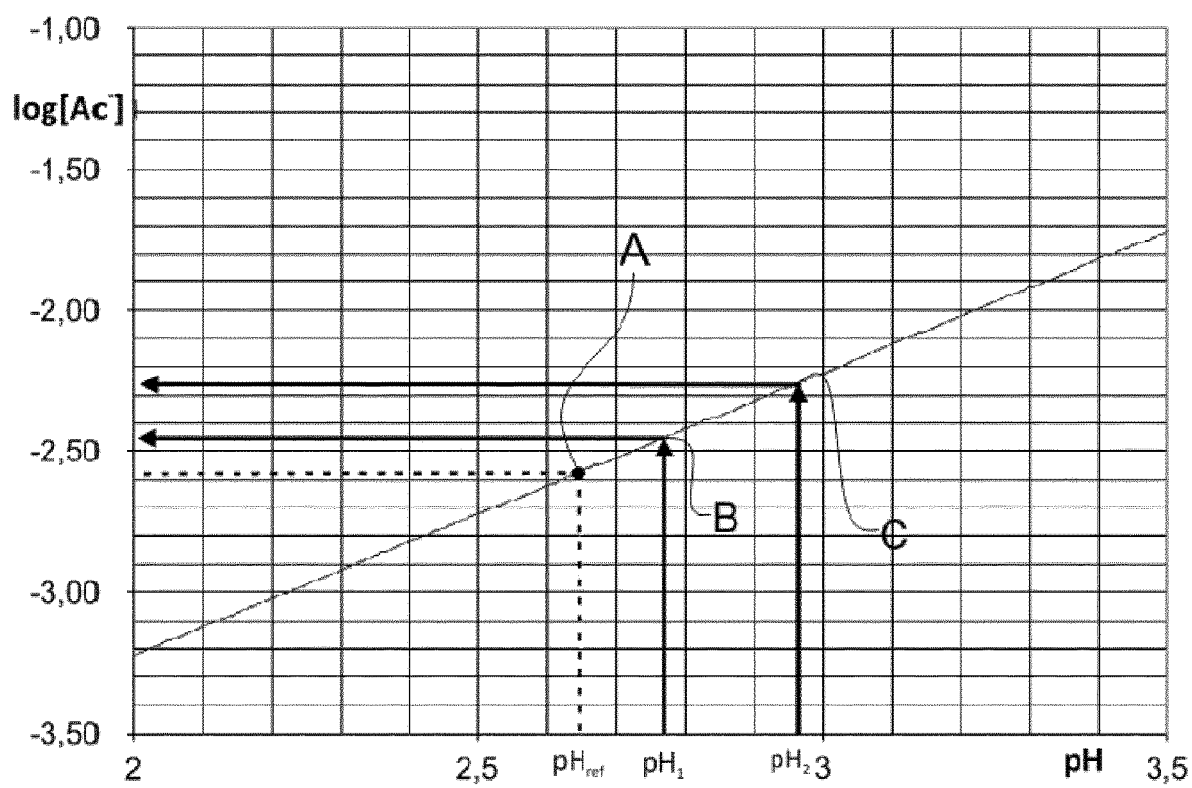
FIG. 1 shows an example of a calibration curve for calculating the amount of strong acid to be added to a sample solution containing a film forming amine for pH adjustment.

The inner surfaces of pipelines, tubes and boilers in industrial plants are treated or coated using additives such as film-forming amines to prevent the surfaces from corrosion. The film forming amines are preferably polyamines or monoamines, such as fatty amines, which are represented by the formula R—(NH—$R^1$)$_n$—$NH_2$, wherein R is an alkyl having 12 to 24 carbon atoms, $R^1$ is methylene or alkylene having 2 to 4 carbon atoms, and n is an integer from 0 to 7.

Preferably, the film forming amines are used as an additive to a processing liquid, wherein the liquid is feed water or industrial water. Specifically, the film forming amines are effective as a corrosion inhibitor forming very thin films on the inner surface of the components and tubings of the water-steam cycle of a nuclear power plant. Preferably, therefore, the film forming amines are injected as an additive into the processing liquid flowing though the water-steam cycle of a nuclear power plant, and in particular the feed water for the water-steam cycle.

The concentration of the film forming amine in the liquid is determined by adding a reagent to a sample of the liquid to form a colored complex of the amine and the reagent, and the colored complex is measured photometrically. The reagent used to form the colored complex with the amine is preferably a xanthene dye, more preferably a xanthene dye selected from the group consisting of fluoresceine, eosin, rose bengal, and Phloxine B.

Most preferably, the reagent is Phloxine B. Phloxine B is also known as cyanosin or the IUPAC name disodium 2',4',5',7'-tetrabromo-4,5,6,7-tetrachloro-3-oxospiro[2-benzofuran-1,9'-xanthene]-3',6'-diolate, and has an absorption maximum at 546-550 nm.

In order to perform the concentration measurement, an aqueous buffer solution of a weak acid and a strong acid is provided, wherein the weak acid has a pKa≥4.5, and the strong acid has a pKa≤1. Preferably, the weak acid is acetic acid, and the strong acid is hydrochloric acid.

An aliquot of the buffer solution is diluted with a given volume of water, and the pH of said diluted buffer solution is determined. Preferably, the pH of the diluted buffer solution is controlled to be in a range of from 2.5 to 2.9, preferably from 2.7 to 2.8.

Thereafter, a given amount of the reagent is added to said diluted buffer solution, and the initial absorbance of said diluted buffer solution containing the reagent is measured. The initial absorbance of the diluted buffer solution can be measured using a commercially available photometer, or the diluted stock solution containing the reagent can be prepared and measured using the above described device for determining a film forming amine in a liquid.

Next, a sample solution is prepared by adding a given volume of the liquid containing the film forming amine to an aliquot of the buffer solution and measuring the pH of the sample solution. Preferably, the volume of the liquid containing the film forming amine corresponds to the volume of water added to form the diluted buffer solution, and the aliquots of the buffer solution used to provide the diluted buffer solution and the sample solution have the same volume.

Since the processing liquid containing the film forming amine is an alkaline solution having a pH>7, the pH of the diluted buffer solution and the sample solution will be different due to neutralization of the film forming amine and optionally other amines present in the liquid by the weak or strong acid of the buffer solution. According to the invention, therefore, the pH of the sample solution is adjusted to match with the pH of the diluted buffer solution by adding a calculated amount of the strong acid.

Preferably, the amount of the strong acid to be added to the sample solution is calculated using a first calibration curve or an algorithm based on the formula:

$$\log[Ac^-] = \log([HAc]_{total}/K_{HAc}) + pH_{sample}$$

wherein
[$Ac^-$] is the anion concentration of dissociated weak acid in the solution,
[$HAc$]$_{total}$ is the total concentration of the weak acid in the solution,
$K_{HAc}$ is the association constant of the weak acid, and
$pH_{sample}$ is a measured pH of the solution.

It is understood by the person skilled in the art that the above formula is valid under the condition that $K_{Hac}[H^+] \gg 1$.

FIG. 1 shows a calibration curve wherein the logarithm of the anion concentration of the dissociated weak acid is specified as function of the pH value. Point A indicates the situation of the diluted buffer solution. The vertical dotted line indicates the pH value of the diluted buffer solution ($pH_{ref}$). The dashed horizontal line indicates the anion concentration of the weak acid at $pH_{ref}$ and a selected total concentration (logarithmic) of the weak acid.

The vertical arrows to points B and C simulate the measured pH value in exemplary sample solutions containing the film forming amine, optionally together with ammonia, ethanolamine, morpholine or other amines. The pH measurement is carried out using the same volume for the diluted buffer solution and the sample solution, respectively. Due to the partial neutralization of the weak acid, the pH value of the sample solution ($pH_1$ or $pH_2$) is higher than $pH_{ref}$. This corresponds to a higher value of the anion concentration of the weak acid $[Ac^-]$ in the sample solutions as compared to the diluted buffer solution, which is indicated in FIG. 1 by means of the horizontal arrows from points B and C.

On the basis of the measured pH value of the sample solution, e.g. $pH_1$ or $pH_2$ in FIG. 1, the increase in the anion concentration of the weak acid can be determined for each sample solution via the calibration curve, and thus the total amine content can also be determined.

After de-logarithmizing, the amount of the strong acid is obtained which must be added to the sample solution in order to match the pH of the sample solution with the reference pH value $pH_{ref}$ of the diluted buffer solution. The advantage of this method step is that only a short pH adjustment is required since it is not necessary to titrate the solutions up to a target pH value.

The amount of the film-forming amine in the sample solution is then determined by means of a photometric measurement. According to the invention, a given amount of the reagent is added to the pH adjusted sample solution to form the colored complex of the film forming amine and the reagent, and the absorbance of the pH adjusted sample solution containing the reagent and the colored complex is measured using a commercial photometer.

Preferably, the concentration of the film forming amine in the processing liquid is calculated from the measured absorbance of the pH adjusted sample solution containing the reagent and the colored complex using a second calibration curve or an algorithm based on the formula $$[\text{Amine}] = (A_{sample} - A_o)/f;$$

wherein
  [Amine] is the concentration of the film forming amine in the solution,
  $A_{sample}$ is the measured absorbance of the solution,
  $A_o$ is the measured initial absorbance of the diluted buffer solution containing the reagent, and
  f is a factor corresponding to the slope of the calibration curve and includes the optical path length and the molar extinction coefficient specific to the reagent and the measuring cell.

The second calibration curve can be obtained by measuring the absorbance of a number of sample solutions containing the reagent and the colored complex at a given pH value, and containing a known amount of the film forming amine.

Preferably, the photometric measurement is carried out semi-automatically or automatically. Further, it is also possible to correct the measured absorbance of the sample solution containing the reagent and the colored complex as a function of the pH value of the solution by means of a software integrated into the photometer, in order to account for any difference of the pH value of the sample solutions used to obtain the second calibration curve.

Figure 2:
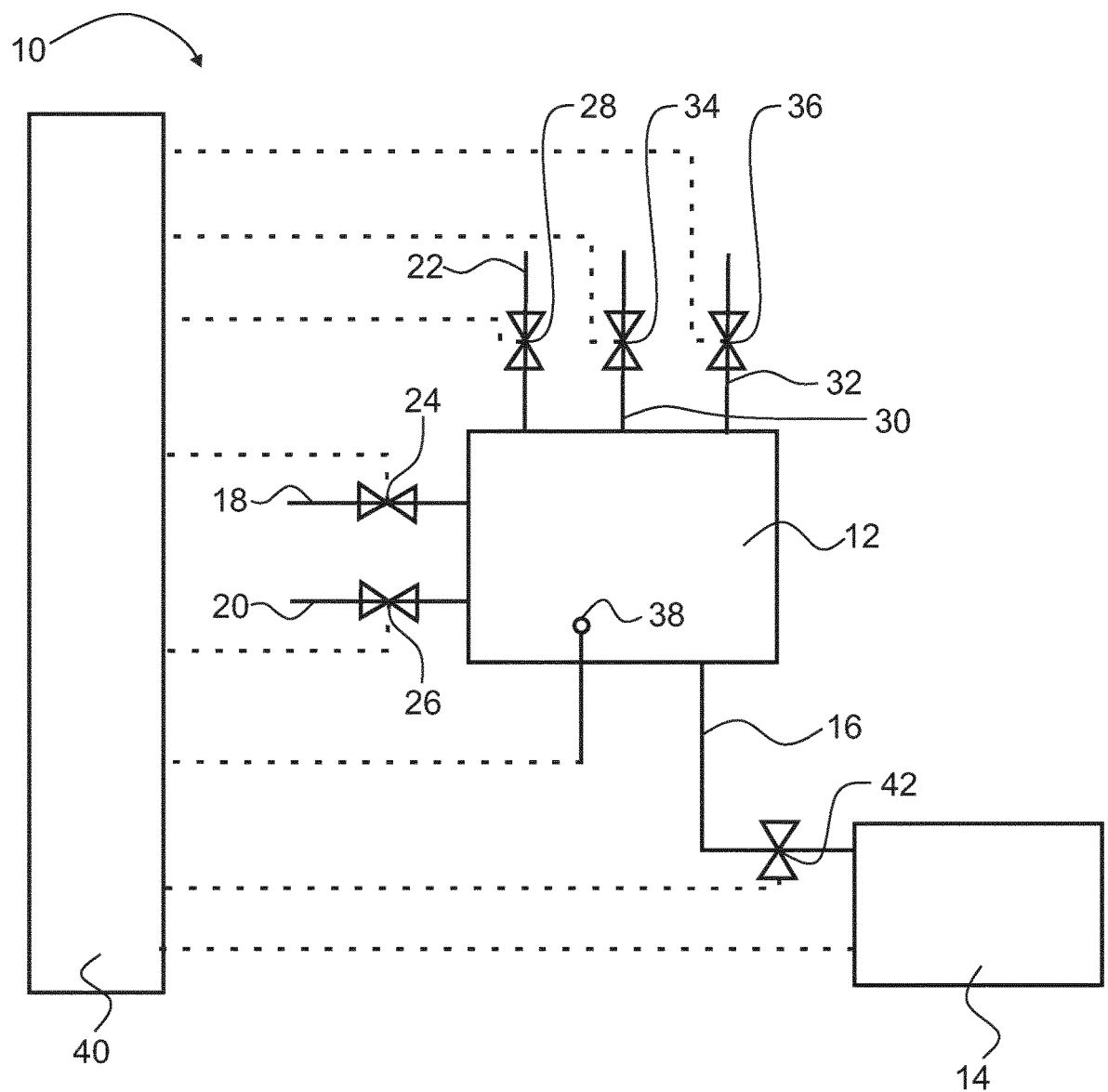
FIG. 2 shows a schematic view of an on-line measuring device for performing the method of the invention.

FIG. 2 shows a schematic representation of a measuring device 10 which can be used to perform the method of the present invention. The device 10 comprises a mixing chamber 12 and a photometer 14 connected to the mixing chamber via a conduit 16. The mixing chamber 12 comprises an inlet line 18 for the buffer solution, an inlet line 20 for the processing liquid and an inlet line 22 for the reagent solution. The amount of the buffer solution, the processing liquid and the reagent solution flowing into the mixing chamber 12 is controlled by means of dosing valves 24, 26, and 28 arranged in the inlet lines 18, 20 and 22. In addition, the mixing chamber 12 is connected to a feedstock for the strong acid and water via supply lines 30, 32 which are equipped with dosing valves 34 and 36. A pH sensor 38 is provided in the mixing chamber. The dosing valves 24, 26, 28, 34, 36, the pH sensor 38 and the photometer 14 are connected to a control unit 40.

The inlet line 20 for the processing liquid can be connected to one or more measuring points (not shown) at a bypass in the steam-water cycle of a nuclear power plant. Connecting the inlet line 20 directly to the measuring point allows for a continuous monitoring of the free film forming amine in the processing liquid present in the water-steam cycle.

In order to obtain the reference values required for pH adjustment of the sample solution and the absorbance of the colored complex, the pH value of the diluted buffer solution is determined and preferably entered into the control unit 40. A given amount of the reagent is added to the diluted buffer solution, and water is added to provide a target volume of the diluted buffer solution containing the reagent. The diluted buffer solution containing the reagent is then transferred to the measuring cell of a photometer to measure the initial absorbance of the reagent in the diluted buffer solution.

The measurement of the reference pH value of the diluted buffer solution and the initial absorbance can be performed using the device of FIG. 2. Preferably, however, the measurement is performed using external measurement devices. The reference values obtained by these measurements are preferably used as input parameters for the control unit 40.

For determining the concentration of a film forming amine in the processing liquid, the control unit 40 operates dosing valves 24, 26 in the inlet lines 18, 20 to introduce a predetermined amount of the processing liquid and the buffer solution into the mixing chamber 12 to form the sample solution. The amount of the processing liquid used to form the sample solution is the same as the amount of water used to prepare the diluted buffer solution. The pH value of the sample solution is measured in the mixing chamber 12 by means of the pH sensor 38. The control unit 40 then compares the measured pH value of the sample solution to the reference pH value of the diluted buffer solution, and calculates the amount of strong acid which must be added to the sample solution to match the pH value of the sample solution with the reference pH value of the diluted buffer solution. Thereafter, control unit 40 provides a signal to the dosing valves 34, 36, and the calculated amount of strong acid and water are introduced into the sample solution.

After pH adjustment of the sample solution, the control unit 40 operates the dosing valve 28 in the inlet line 22 for the reagent solution, and the reagent is mixed with the sample solution in the mixing chamber 12 to form the colored complex of the film forming amine and the reagent. The amount of reagent added to the sample solution corresponds to the amount of the reagent in the diluted buffer solution so that the concentration of the reagent is the same in both solutions.

The sample solution containing the reagent and the colored complex is then transferred to the photometer 14 via conduit 16 preferably by operating dosing valve 42 in the conduit 16, and the absorbance of the solution is measured.

The control 40 unit then calculates the amount of the film forming amine in the processing liquid from the measured absorbance by comparing the measured absorbance of the sample solution containing the reagent and the colored complex to a calibration curve obtained from measuring the absorbance of a number of reference solutions containing the reagent and the colored complex as well as a known amount of the film forming amine at the given pH value.

The control unit 40 can also include a software for correcting the measured absorbance as a function of the pH value of the pH adjusted sample solution. In order to perform this correction, the initial absorbance is measured at a number of reference pH values within the range of from 2.5 to 2.9, and a factor is applied to the measured absorbance to account for the difference between the pH value of the reference solutions used to obtain the second calibration curve and the actual pH value of the pH adjusted sample solution.

DESCRIPTION OF A PREFERRED EMBODIMENT

The following is a practical example to illustrate the photometric measurement of a film forming amine in a sample solution, without pH adjustment.

The reagent solution is prepared by dissolving 41.45 mg of Phloxine B in 80 ml of water, and filling up with water to 100 ml to provide a 0.5 mM aqueous solution of Phloxine B.

A buffer solution of acetic acid and hydrochloric acid is provided by dissolving 120 g glacial acetic acid in 100 mL of water, adding 10 mL of 0.1 M hydrochloric acid, and filling up with water to obtain 1 liter of the buffer solution.

10 mL of the buffer solution are provided, and 40 mL of the processing liquid containing the film forming amine are added to obtain a total of 50 mL of the sample solution.

The initial absorbance of the reagent is determined by mixing 5 mL of the buffer solution with 20 mL of water to obtain a diluted buffer solution and adding 5 mL of the 0.5 mM reagent solution to the diluted buffer solution. The diluted buffer solution mixed with the reagent solution is transferred to the measuring cell of a photometer, and the initial absorbance is measured at a wavelength of between 400 to 600 nm.

The absorbance of the sample solution containing the reagent and the colored complex is determined by fast mixing 25 mL of the sample solution with 5 mL of the reagent solution, and measuring the absorbance of the mixed solution in the photometer. A measuring cell having an optical path length of 1 cm will be suitable if the concentration of the film forming amine in the processing liquid is in a range of from 80 ppb to 10 ppm. Use of a measuring cell having an optical path length of 5 cm is useful if the concentration of the film forming amine in the processing liquid is lower, down to about 20 ppb.

The measured absorbance is compared to the second calibration curve, and the concentration of the film forming amine in the processing liquid is obtained from the calibration curve, either manually or by way of an algorithm. The second calibration curve is obtained from measuring the absorbance of a number of reference solutions containing the reagent and the colored complex as well as a known amount of the film forming amine at the given pH value under the same conditions as used for the sample solution.

As an example, the concentration [FFA] of a film forming amine in the sample of the processing liquid (in ppm) can be calculated from the formula $$[FFA] = (A_{sample} - A_0)/f$$

wherein $A_{sample}$ is the measured absorbance, $A_0$ is the initial absorbance, and the factor "f" is empirically obtained from the second calibration curve for reference sample solutions having a pH of 2.7.

For the adjustment of the pH value of the sample solution to match with the pH of the diluted buffer solution, 40 mL of water are added to 8 mL of the buffer solution, and the reference pH value of the diluted buffer solution is determined. Thereafter, 2 mL of water are added to adjust the volume of the diluted buffer solution to a target volume of 50 mL, and 5 ml of the reagent solution are added to 25 mL of the diluted buffer solution as described above.

Next, 40 mL of the processing liquid are added to 8 mL of the buffer solution of acetic acid and hydrochloric acid to provide the sample solution, and the pH value of the sample solution is determined. The first calibration curve or algorithm described above is used to determine the amount of hydrochloric acid which is to be added to the sample solution so that the pH of the sample solution is lowered to match with the reference pH value of the diluted buffer solution, and the calculated amount of hydrochloric acid is added. Water is used to fill up the volume of the pH adjusted sample solution to the target volume of 50 mL.

After the pH of the sample solution is adjusted to match with the reference pH value of the diluted buffer solution, 5 mL of the reagent solution is added to 25 mL of the pH adjusted sample solution, and the absorbance of the sample solution containing the reagent and the colored complex is measured. The concentration of the film forming amine in the processing liquid can then be calculated from the measured absorbance using the second calibration curve, as described above.

Although the invention is illustrated and described herein as embodied in a method and device for determining a film forming amine in a liquid, it is not intended to be limited to the details shown, since various modifications and structural changes may be made therein without departing from the scope of the appended claims.

The invention claimed is:

1. A method for the determination of a concentration of a film forming amine in a liquid by adding a reagent to the liquid to form a colored complex of the amine and the reagent, wherein the colored complex is measured photometrically, the method comprising the steps of:
   a) Providing a buffer solution of a weak acid having a $pKa \geq 4.5$ and a strong acid having a $pKa \leq 1$;
   b) Diluting an aliquot of the buffer solution with a given volume of water, and determining a pH value of said diluted buffer solution;
   c) Adding a given amount of said reagent to said diluted buffer solution and measuring an initial absorbance of said diluted buffer solution containing the reagent;

d) Preparing a sample solution by adding a given volume of the liquid containing the film forming amine to an aliquot of the buffer solution and measuring a pH value of the sample solution;

e) Adjusting the pH value of the sample solution to match with the pH value of the diluted buffer solution by adding a calculated amount of the strong acid, wherein the amount of the strong acid to be added to the sample solution is calculated using a first calibration curve or an algorithm based on the formula:

$$\log[Ac^-]=\log([HAc]_{total}/K_{HAc})+pH_{sample},$$

wherein

[$Ac^-$] is an anion concentration of dissociated weak acid in the sample solution,

[$Hac$]$_{total}$ is a total concentration of the weak acid in the sample solution, $K_{HAc}$ is an association constant of the weak acid, and $pH_{sample}$ is a measured pH of the sample solution; and f) Adding a given amount of said reagent to the pH adjusted sample solution to form the colored complex and measuring an absorbance of the pH adjusted sample solution containing the reagent and the colored complex, wherein the concentration of the film forming amine in the liquid is calculated from the measured absorbance of the pH adjusted sample solution containing the reagent and the colored complex using a second calibration curve or an algorithm based on the formula:

$$[Amine]=(A_{sample}-A_o)/f;$$

wherein

[Amine] is the concentration of the film forming amine in the pH adjusted sample solution, $A_{sample}$ is the measured absorbance of the pH adjusted sample solution containing the reagent and the colored complex, $A_o$ is the measured initial absorbance of the diluted buffer solution containing the reagent, and f is a factor corresponding to a slope of the second calibration curve.

2. The method of claim 1 wherein the film forming amine is represented by the formula $R-(NH-R^1)_n-NH_2$, wherein R is an alkyl having 12 to 24 carbon atoms, $R^1$ is methylene or alkylene having 2 to 4 carbon atoms, and n is an integer from 0 to 7.

3. The method of claim 1 wherein the liquid is feed water or industrial water.

4. The method of claim 1 wherein the reagent is a xanthene dye.

5. The method of claim 4 wherein the xanthene dye is fluorescein, eosin, rose bengal, or Phloxine B.

6. The method of claim 5 wherein the xanthene dye is Phloxine B.

7. The method of claim 1 wherein the weak acid is acetic acid, and wherein the strong acid is hydrochloric acid.

8. The method of claim 1 wherein the pH of the diluted buffer solution is from between 2.5 to 2.9.

9. The method of claim 1 wherein the method is carried out manually or semi-automatically.

10. A device for determining an amount of a film forming amine using the method of claim 1, wherein the device comprises:

a mixing chamber and a photometer connected to the mixing chamber;

a pH sensor provided in the mixing chamber; and a control unit connected to the mixing chamber and the photometer and being configured to perform the steps of claim 1;

wherein the mixing chamber is connected to a feedstock of a strong acid and water, and further comprises an inlet line for a buffer solution, an inlet line for a processing liquid and an inlet line for a reagent solution; and wherein the control unit comprises means for controlling an amount of the buffer solution, the processing liquid and the reagent solution supplied to the mixing chamber, as well as means for calculating and introducing an amount of the strong acid and water into the mixing chamber based on an input signal received from the pH sensor, wherein the amount of the strong acid to be added to a sample solution in the mixing chamber is calculated using a first calibration curve or an algorithm based on the formula:

$$\log[Ac^-]=\log([HAc]_{total}/K_{HAc})+pH_{sample},$$

wherein

[$Ac^-$] is an anion concentration of dissociated weak acid in the sample solution,

[$HAc$]$_{total}$ is a total concentration of the weak acid in the sample solution, $K_{HAc}$ is an association constant of the weak acid, and $pH_{sample}$ is a measured pH of the sample solution;

and wherein the control unit further comprises means for calculating an amount of a film forming amine in the processing liquid based on an input signal received from the photometer, wherein the amount of the film forming amine in the liquid is calculated from the measured absorbance of the pH adjusted sample solution containing the reagent and the colored complex using a second calibration curve or an algorithm based on the formula:

$$[Amine]=(A_{sample}-A_o)/f;$$

wherein

[Amine] is the amount of the film forming amine in the pH adjusted sample solution, $A_{sample}$ is the measured absorbance of the pH adjusted sample solution containing the reagent and the colored complex, $A_o$ is the measured initial absorbance of the diluted buffer solution containing the reagent, and f is a factor corresponding to a slope of the second calibration curve.

* * * * *